(12) United States Patent
Cullen et al.

(10) Patent No.: US 9,144,679 B2
(45) Date of Patent: Sep. 29, 2015

(54) SYSTEM AND METHOD FOR DEFINING STIMULATION PROGRAMS INCLUDING BURST AND TONIC STIMULATION

(71) Applicant: Advanced Neuromodulation Systems, Inc., Plano, TX (US)

(72) Inventors: Patrick M. Cullen, Dallas, TX (US); John H. Erickson, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 154 days.

(21) Appl. No.: 13/716,968

(22) Filed: Dec. 17, 2012

(65) Prior Publication Data

US 2013/0211477 A1 Aug. 15, 2013

Related U.S. Application Data

(63) Continuation of application No. 12/423,124, filed on Apr. 14, 2009, now Pat. No. 8,340,775.

(60) Provisional application No. 61/044,680, filed on Apr. 14, 2008.

(51) Int. Cl.
*A61N 1/00* (2006.01)
*A61N 1/36* (2006.01)
*A61N 1/05* (2006.01)
(Continued)

(52) U.S. Cl.
CPC ............. *A61N 1/36128* (2013.01); *A61N 1/05* (2013.01); *A61N 1/36178* (2013.01); *A61N 1/37247* (2013.01); *G06F 19/3406* (2013.01); *A61N 1/0553* (2013.01)

(58) Field of Classification Search
CPC . A61N 1/36; A61N 1/37247; A61N 1/37252; A61N 1/36128; A61N 1/05; A61N 1/36178; G06F 19/3406
USPC .............. 607/45, 46, 68–71, 30, 32, 59
See application file for complete search history.

(56) References Cited

U.S. PATENT DOCUMENTS 6,622,048 B1 9/2003 Mann et al.
6,748,276 B1 6/2004 Daignault, Jr. et al.
6,944,501 B1 9/2005 Pless
(Continued)

FOREIGN PATENT DOCUMENTS

WO 0193953 12/2001

*Primary Examiner* — Niketa Patel
*Assistant Examiner* — Lindsey G Hankins

(57) ABSTRACT

In one embodiment, a method for defining a stimulation program for electrical stimulation of a patient, the method comprising: providing a single screen user interface that comprises a first plurality of controls and a second plurality of controls, the first plurality of controls allowing selection of multiple stimulation parameters for a plurality of stimulation sets, the second plurality of controls allowing selection of multiple stimulation parameters defining burst stimulation and tonic stimulation; receiving user input in one or more of the second plurality of controls; and automatically modifying parameters for one or more stimulation sets in response to receiving the user input in one or more of the second plurality of controls and modifying values displayed in one or more controls of the first plurality of controls according to the modified parameters, the modified parameters reflecting a stimulation program that includes an interleaved pattern of burst stimulation and tonic stimulation for delivery to the patient.

7 Claims, 5 Drawing Sheets

(51) Int. Cl.
*A61N 1/372* (2006.01)
*G06F 19/00* (2011.01)

(56) References Cited

U.S. PATENT DOCUMENTS

| | | | |
|---|---|---|---|
| 6,950,706 | B2 | 9/2005 | Rodriguez et al. |
| 7,117,034 | B2 | 10/2006 | Kronberg |
| 2003/0120323 | A1 | 6/2003 | Meadows et al. |
| 2003/0199927 | A1* | 10/2003 | Ousdigian et al. ............ 607/4 |
| 2004/0199217 | A1 | 10/2004 | Lee et al. |
| 2004/0210271 | A1 | 10/2004 | Campen et al. |
| 2006/0095088 | A1 | 5/2006 | DeRidder |
| 2006/0212089 | A1 | 9/2006 | Tass |
| 2006/0247718 | A1 | 11/2006 | Starkebaum |
| 2006/0259097 | A1 | 11/2006 | Hickman et al. |
| 2007/0255336 | A1* | 11/2007 | Herbert et al. ............ 607/40 |

* cited by examiner

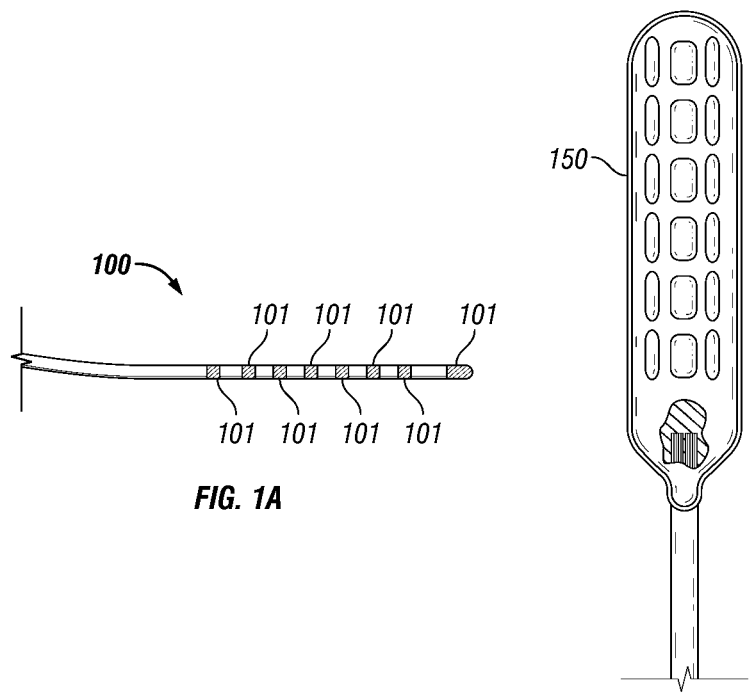
FIG. 1A
FIG. 1B
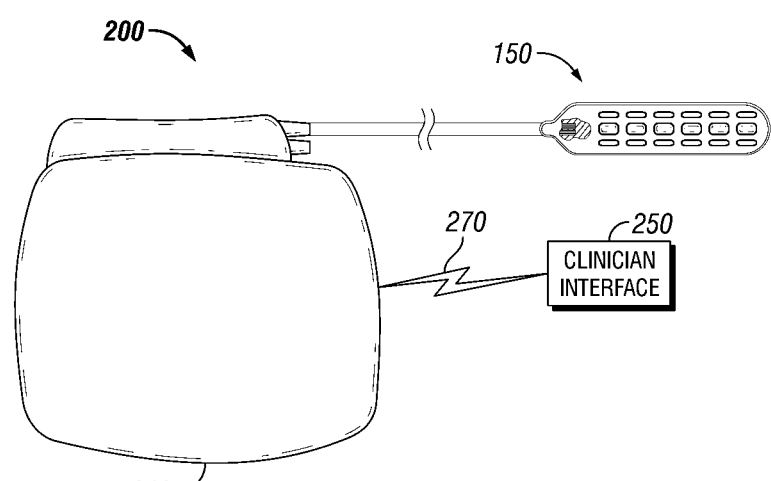
FIG. 2

SYSTEM AND METHOD FOR DEFINING STIMULATION PROGRAMS INCLUDING BURST AND TONIC STIMULATION

CROSS-REFERENCE TO RELATED APPLICATIONS

This application is a continuation of U.S. application Ser. No. 12/423,124, filed Apr. 14, 2009, now U.S. Pat. No. 8,340,775, which claims the benefit of U.S. Provisional Application No. 61/044,680, filed Apr. 14, 2008, the disclosures of which are fully incorporated herein by reference for all purposes.

TECHNICAL FIELD

This application is generally related to systems and methods for creating stimulation programs including burst stimulation and tonic stimulation to treat various neurological disorders or conditions.

BACKGROUND

Different firing modes or frequencies occur in the brain and/or other neuronal tissue, for example tonic firing and burst firing (irregular or regular burst firing). Such firing modes can be utilized for normal processing of information, however, alteration of the firing modes, may also lead to pathology.

For example, certain neurological conditions are associated with hyperactivity of the brain and can be traced to a rhythmic burst firing or high frequency tonic firing (e.g., tinnitus, pain, and epilepsy). Other conditions can be associated with an arrhythmic burst firing or a desynchronized form of tonic and burst firing (e.g., movement disorders and hallucinations).

During the past decade, neuromodulation systems have been used to modulate various areas of the brain, spinal cord, or peripheral nerves (see, for example, U.S. Pat. Nos. 6,671,555; 6,690,974). These types of systems utilize tonic forms of electrical stimulation. Recently burst transcranial magnetic stimulation (TMS) at theta frequencies has been developed. Theta burst TMS has been shown to produce an effect on motor and visual cortex by suppressing excitatory circuits after a short application period of only 20-190 s.

SUMMARY

In one embodiment, a method for defining a stimulation program for electrical stimulation of a patient, the method comprising: providing a single screen user interface that comprises a first plurality of controls and a second plurality of controls, the first plurality of controls allowing selection of multiple stimulation parameters for a plurality of stimulation sets, the second plurality of controls allowing selection of multiple stimulation parameters defining burst stimulation and tonic stimulation; receiving user input in one or more of the second plurality of controls; and automatically modifying parameters for one or more stimulation sets in response to receiving the user input in one or more of the second plurality of controls and modifying values displayed in one or more controls of the first plurality of controls according to the modified parameters, the modified parameters reflecting a stimulation program that includes an interleaved pattern of burst stimulation and tonic stimulation for delivery to the patient.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIGS. 1A and 1B respectively depict conventional percutaneous and paddle leads that may be utilized to deliver burst and tonic stimulation patterns according to some embodiments.

FIG. 2 depicts a stimulation system that can be used to deliver burst and tonic stimulation according to some embodiments.

DETAILED DESCRIPTION

Figure 3:
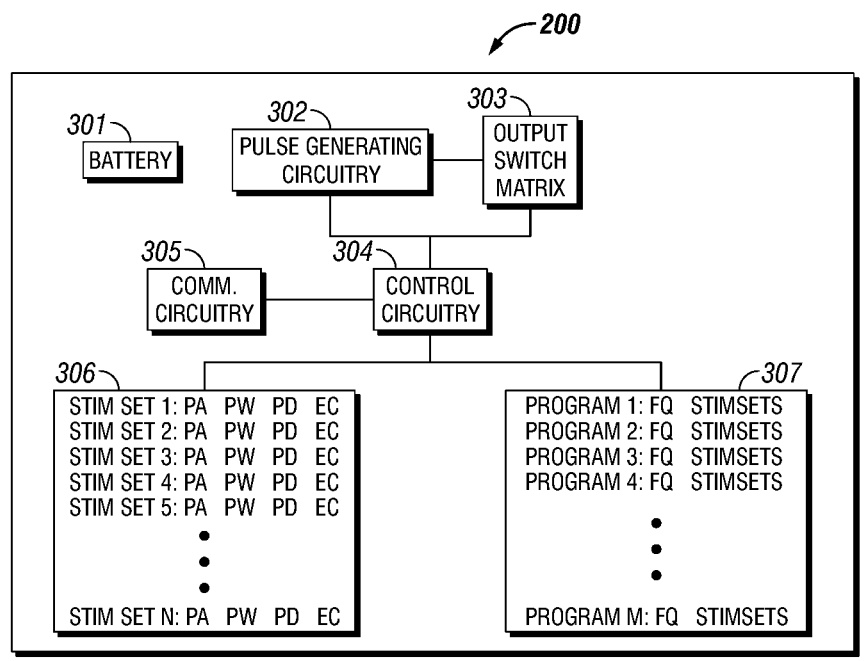
FIG. 3 depicts a block diagram of an implantable pulse generator that can be programmed to generate burst and tonic stimulation according to some embodiments.

As used herein, the term "stimulate" or "stimulation" refers to electrical, and/or magnetic, stimulation that modulates one or more neuronal sites.

As used herein, the term "tonic stimulation" refers to a stimulation pattern in which individual pulses occur with relatively long inter-spike intervals or equivalently at relatively lower frequencies. The inter-spike intervals for tonic stimulation are sufficiently long that significant temporal summation of cellular depolarizations does not occur.

As used herein, "burst stimulation" refers to pulses generated by a pulse generator that is similar to burst firing of action potentials within neural tissue. Specifically, burst stimulation includes multiple discrete bursts with each burst comprising multiple pulses or spikes. Burst stimulation may occur from a plateau or elevated pulse amplitude applied by the pulse generator. Also, a hyper-polarizing or other pre-conditioning pulse may precede the burst. A charge balancing pulse or pulses may be applied within the burst or at the end of the burst. Within an individual burst of electrical pulses, the pulses are separated from each adjacent pulse by an inter-pulse interval. The inter-pulse interval can be about 0.5 microseconds to about 10 milliseconds. The intra-burst spike rate does not necessarily occur at a fixed rate and can be variable within an individual burst. The period of time between two bursts is referred to as the "inter-burst interval." The inter-burst interval may not be affected by the presence of any number of tonic spikes located anywhere within a series of two or more bursts.

The combination of burst stimulation and tonic stimulation in a stimulation pattern is believed to offer benefits for a number of neurological conditions or disorders that were not previously achievable using conventional stimulation techniques.

For example, tinnitus is an auditory phantom percept related to reorganization and hyperactivity of the auditory system. The auditory system consists of two main parallel pathways supplying auditory information to the cerebral cortex: the topographically organized lemniscal (classical) system, and the non-topographic extralemniscal (non-classical) system. The classical pathways use the ventral thalamus, the neurons of which project to the primary auditory cortex whereas the non-classical pathways use the medial and dorsal thalamic nuclei that project to the secondary auditory cortex and association cortices, thus bypassing the primary cortex. While neurons in the classical pathways only respond to one modality of sensory stimulation, many neurons in the non-classical pathway respond to more than one modality. Neurons in the ventral thalamus fire in a tonic or semi-tonic mode while neurons in the medial and dorsal thalamus fire in bursts. The non-classical pathways receive their input from the classical pathways, which means that the ascending auditory pathways are a complex system of at least two main parallel systems that provide different kinds of processing and which interact with each other in a complex way. Both systems provide sensory input to the amygdala through a long cortical route, and in addition, the non-classical pathways provide subcortical connections to the lateral nucleus of the amygdala from dorsal thalamic nuclei.

Studies in humans have indicated that some patients with tinnitus have an abnormal activation of the non-classical auditory system. Studies of animal models of tinnitus have shown that burst firing is increased in the non-classical system and tonic firing activity is increased in the classical system. Interestingly, not only tonic firing but also burst firing is increased in neurons in the primary auditory cortex in animal models of tinnitus. Studies in patients with intractable tinnitus have shown that tonic electrical stimuli of the primary and secondary auditory cortex can suppress pure tone tinnitus, but not white noise/narrow band noise tinnitus.

It has been hypothesized that noise-like tinnitus may be caused by increased burst firing in the non-topographic (extralemniscal) system, whereas pure tone tinnitus may be the result of increased tonic firing in the topographic (lemniscal) system. Transcranial magnetic stimulation (TMS), a non-invasive tool, was shown to modulate the neuronal activity of the auditory cortex thereby modulating the perception of tinnitus. It has been demonstrated that tonic stimulation can suppress pure tone tinnitus, but not narrow band noise, whereas burst TMS can suppress narrow band or white noise tinnitus (noise-like).

In the clinical setting, cases of tinnitus are commonly complex in that the patient suffers from more than one type (i.e. pure tone, narrow band, white noise) of tinnitus in one or both ears. It is believed that only one of tonic mode stimulation and burst mode stimulation is not capable of alleviating the symptoms for such patients.

To determine the ability of the combination of burst and tonic stimulation to treat tinnitus symptoms, four patients with both unilateral noise-like and pure tone (VR) tinnitus were implanted with electrodes for stimulation therapy using both tonic and burst stimulation parameters. In three patients, the stimulation leads (Lamitorode 44 stimulation lead available from ANS Medical, Plano, Tex., USA) were implanted adjacent to the auditory cortex, and one patient was implanted with a cervical dorsal column stimulation lead (Lamitrode 44 stimulation lead). All patients underwent burst stimulation at 6, 18, or 40 Hz consisting of 5 spikes with 1 ms pulse width, 1 ms interspike interval in a charged balanced manner and 6, 18, or 40 Hz tonic mode interspersed between or around the bursts. The stimuli were delivered by an 8 channel digital neurostimulator (DS8000, World Precision Instruments, Hertfordshire, England/Sarasota, Fla., USA), capable of delivering tonic and burst mode stimulation.

If the patients benefited from the stimulation, a commercially available IPG capable of burst mode was implanted (EON® implantable pulse generator from ANS Medical, Plano, Tex., USA), programmed with similar settings, using a programmer. The only difference to the stimuli delivered with the external stimulator and the EON® implantable pulse generator, was the ramping used with the EON® implantable pulse generator (FIG. 2). The ramping characteristics of the burst pulses were chosen to model naturally occurring burst firing as closely as possible.

The below Table 1 shows that by using a combination of tonic and burst stimulation parameters patients suffering from pure tone and noise-like tinnitus can be treated. The tonic and burst stimulation can be combined on the same poles or center tone or surrounding the burst stimulation with tonic stimulation.

TABLE 1

| Patient | Freq | Burst | Tonic | Intra-Burst Spike Rate | Spikes # | Suppression of Tinnitus |
|---|---|---|---|---|---|---|
| PB (DC) | 6 Hz | Yes | Yes | 500 Hz | 5 | 95% |
| RM (AC) | 40 Hz | Yes | Yes | 500 Hz | 5 | 100% |
| DA (AC) | 40 Hz | Yes | Yes | 500 Hz | 5 | 90% |
| VR (AC) | 18 Hz | Yes | Yes | 500 Hz | 5 | 90% |

Thus, in cases of complex tinnitus combinations of burst and tonic mode stimulation were shown to effectively reduce the occurrence and severity of symptoms. Although tonic mode stimulation alone is sufficient to reduce symptom occurrence and severity in many simple cases of pure tone tinnitus, the symptoms are rarely completely abolished. Moreover, in many cases where symptoms are reduced, the effect of tonic mode stimulation is relatively short lasting and repeated treatments result in significantly reduced efficacy over time. Stimulation protocols combining burst and tonic mode stimulation are significantly more effective at reducing symptoms in patients suffering from pure tone tinnitus, the effects of a single treatment last longer, and there is no significant reduction in efficacy with repeated treatment. Yet further, the combination of burst and tonic stimulation is effective at reducing the symptoms or severity of patients that suffer from both pure tone tinnitus and noise-like tinnitus. Yet further, the combination of burst and tonic stimulation can act as an anti-habituation protocol.

In view of the above results for the combination of burst and tonic stimulation, one of skill in the art can realize that such stimulation protocols can be used to treat neurological diseases/disorders having both a topographic (lemniscal system) and the non-topographic system (extralemniscal system) component. One such exemplary disease/disorder may include chronic pain. For example, typically, tonic stimulation is used to treat chronic pain. Tonic stimulation alters the topographic or lemniscal system resulting in the treatment of chronic pain. The downside to using tonic stimulation to treat chronic pain is that typically the pain may be replaced with paresthesias, which acts through the non-topographic system. Thus, an alternative to treat chronic pain without paresthesias may be to utilize a stimulation protocol that employs both burst and tonic stimulation, thereby altering both the non-topographic and the topographic system to result in treatment of chronic pain.

Yet further, another advantage of this type of combination protocol is the ability of this combination of stimulation to reduce and/or prevent anti-habituation or anti-adaptation of electrical stimulation. Those of skill in the art are aware of the problem that occurs with continual electrical stimulation in that the brain may adapt to the stimulation and the protocol is no longer effective to treat the symptoms. Thus, a combination protocol as described herein can alleviate this type of adaptation and or habituation.

Burst and tonic stimulation can be applied to neuronal tissue of a patient using any known or later developed stimulation lead such as percutaneous leads and paddle leads. As shown in FIG. 1A, a percutaneous lead 100 typically has two or more equally-spaced electrodes 101 which are placed above the dura layer through the use of a Touhy-like needle. For insertion, the Touhy-like needle is passed through the skin between desired vertebrae to open above the dura layer. A commercially available example of an eight-electrode percutaneous lead is the OCTRODE® lead manufactured by Advanced Neuromodulation Systems, Inc. Electrodes 101 emit electrical stimulation energy generally radially (i.e., generally perpendicular to the axis of stimulation lead 100) in all directions. In contrast to a percutaneous lead 100, a paddle lead 150 (FIG. 1B) has a paddle configuration and typically possess a plurality of electrodes (for example, two, four, eight, or sixteen) arranged in one or more columns. Electrodes of paddle lead 150 emit electrical stimulation energy in a direction generally perpendicular to the surface of stimulation lead 150 on which they are located. A commercially available example of a paddle lead 150 is the LAMITRODE 44® lead, which is manufactured by Advanced Neuromodulation Systems, Inc.

Referring to FIG. 2, stimulation system 200 can be programmed to generate and deliver burst and tonic stimulation according to one representative embodiment. System 200 comprises implantable pulse generator (IPG) 210, stimulation lead 150, and controller 250. IPG 210 can be coupled to any number or types of stimulation leads directly through the header of IPG 210 or indirectly through one or more "extensions," which are known in the art. In an alternative embodiment, electrodes can be integrated with the housing of IPG 210 and IPG 210 can be implanted directly at the site where stimulation is applied to neuronal tissue.

IPG 210 typically comprises a metallic housing that encloses the pulse generating circuitry, control circuitry, communication circuitry, battery, recharging circuitry, etc. of the device. An example of a commercially available IPG is the EON® IPG available from Advanced Neuromodulation Systems, Inc. IPG 210 also typically comprises a header structure for electrically and mechanically coupling to one or more stimulation leads. The electrical pulses generated by IPG 210 are conducted through conductors (not shown) embedded within stimulation lead 150 and delivered to tissue of the patient using electrodes 101 at a distal end of stimulation lead 150.

IPG 210 is preferably adapted to communicate with external devices, such as controller 250, after implantation within a patient. For example, controller 250 may utilize wireless link 270 to communicate with IPG 210 after IPG 210 is implanted within a patient to control the operations of IPG 210. Controller 250 can be implemented by utilizing a suitable handheld processor-based system that possesses wireless communication capabilities. The wireless communication functionality can be integrated within the handheld device package or provided as a separate attachable device. The interface functionality of controller 250 is implemented using suitable software code for interacting with the clinician and using the wireless communication capabilities to conduct communications with IPG 210.

A doctor, another clinician, the patient, or another user may use controller 250 located external to the person's body to provide control signals for operation of IPG 210. In some representative embodiments, controller 250 preferably provides a user interface that is adapted to allow a clinician to efficiently define a stimulation program that includes burst stimulation and tonic stimulation. IPG 210 modifies its internal parameters in response to the control signals to vary the stimulation parameters of stimulation pulses transmitted through stimulation lead 150 to the predetermined neuronal tissue.

IPG 210 can be controlled by the signals from controller 250 to allow the various characteristics of the burst stimulus to be set by a clinician to allow the combination of the burst stimulus and tonic stimulus to be optimized to treat a patient's specific disorder or condition. For example, the spike amplitude, the inter-spike interval, the inter-burst interval, the number of bursts to be repeated in succession, the amplitude of the various pulses, the placement and/or timing of the tonic stimulus in relation to the burst stimulus, the amplitude of the tonic stimulus, the frequency of the tonic stimulus, the ratio of the burst stimulus to the tonic stimulus, altering the charge of the burst and/or tonic stimulus, altering the use of biopolar and/or unipolar or monopolar pulses (e.g., unipolar burst stimulus and bipolar tonic stimulus or bipolar burst stimulus and unipolar tonic stimulus) and other such characteristics could be controlled using respective parameters accessed by the microcontroller during burst stimulus and/or tonic stimulus operations.

Conventional implantable pulse generators devices typically include a microcontroller and a pulse generation module. The pulse generation module generates the electrical pulses according to a defined pulse width and pulse amplitude and applies the electrical pulses to defined electrodes. The microcontroller controls the operations of the pulse generation module according to software instructions stored in the device and accompanying stimulation parameters. According to some embodiments, the control signals provided by controller 250 devices can be selected to cause the microcontroller to deliver a number of spikes (relatively short pulse width pulses) that are separated by an appropriate inter-spike interval. Thereafter, the programming of the microcontroller causes the pulse generation module to cease pulse generation operations. The controls signals provided to the microcontroller also causes a repetition of the spike generation and cessation of operations for a predetermined number of times. After the predetermined number of repetitions have been completed, the microcontroller can cause burst stimulation to cease for an amount of time, deliver a tonic pulse, delay for another amount of time, and repeat the pulse generating process. Also, in some embodiments, the microcontroller could be programmed to cause the pulse generation module to deliver a hyperpolarizing pulse before the first spike of each group of multiple spikes.

FIG. 3 depicts a block diagram of IPG 200 that may be programmed to deliver burst and tonic stimulation in accordance with some representative embodiments. IPG 200 comprises battery 301, pulse generating circuitry 302, output switch matrix 303, control circuitry 304, and communication circuitry 305. Control circuitry 304 controls the generation of pulses by pulse generating circuitry 302 and the delivery of the generated pulses by output switch matrix 303. Specifically, control circuitry 304 controls the amplitude and pulse width of a respective pulse by controlling pulse generating circuitry 302. Additionally, control circuitry 304 controls the timing of the generation of pulses by controlling pulse generating circuitry 302. Control circuitry 304 further configures output switch matrix 303 to control the polarity associated with a plurality of outputs associated with switch matrix 303. In one representative embodiment, control circuitry 304 is implemented using a microcontroller (or other suitable processor) and suitable software instructions stored thereon or otherwise to implement the appropriate system control. Alternatively, control circuitry 304 may comprise an application specific integrated circuit.

Control circuitry 304 preferably controls pulse generating circuitry 302 and output switch matrix 303 using "multi-stim set programs" which are known in the art. As used herein, a "stim set" refers to a set of parameters which define a pulse to be generated and how the pulse is to be delivered. As shown in FIG. 3, a plurality of stim sets 306 are defined in memory of IPG 200. The memory can be integrated with control circuitry 304 or provided separately in IPG 200. Each stim set defines a pulse amplitude, a pulse width, (optionally a pulse delay), and an electrode combination. The pulse amplitude refers to the amplitude for a given pulse and the pulse width refers to the duration of the pulse. The pulse delay represents an amount of delay to occur after the generation of the pulse (equivalently, an amount of delay could be defined to occur before the generation of a pulse). The amount of delay represents an amount of time when no pulse generation occurs. In lieu of providing a delay parameter, another stimset could be defined to provide a "pulse" with zero pulse amplitude to implement delay between other non-zero amplitude pulses. The electrode combination defines the polarities for each output of output switch matrix 303 which, thereby, controls how a pulse is applied via electrodes of a stimulation lead. Other pulse parameters could be defined for each stim set such as pulse type, repetition parameters, etc.

As shown in FIG. 3, IPG 200 comprises a plurality of stimulation programs 307. A stimulation program preferably defines a plurality of pulses to be generated in succession and the frequency of repetition of the pulses. Specifically, when control circuitry 304 executes a stimulation program, control circuitry 304 first retrieves the stimulation parameters for the first stimulation set of the stimulation program. Control circuitry 304 modifies an amplitude setting of pulse generating circuitry 302 according to the amplitude parameter of the stim set. Control circuitry 304 also configures output switch matrix 303 according to the electrode combination of the stim set. Then, control circuitry 304 causes pulse generating circuitry 302 to generate a pulse for an amount of time as defined by the pulse width parameter.

Control circuitry 304 stops the pulse generation and waits an amount of time as defined by a delay parameter (or equivalently by an amount of time defined by a inter-burst frequency parameter) or by an amount of time defined by another stim set in which the pulse amplitude is set to zero. Control circuitry 304 then proceeds to the next stimulation set in the stimulation program and repeats the process. Each stimulation set in the stimulation program is processed in the same manner. When the last stimulation set of the stimulation program is completed, control circuitry 304 waits an amount of time as defined by the frequency parameter of the stimulation program before beginning again. In another implementation, a delay parameter or zero-amplitude stim set can be defined for the end of the stimulation program to cause the stim set program to function at the desired frequency. That is, the total time of execution of one cycle through the stim sets of the program equals the reciprocal of the desired stimulation program frequency. Control circuitry 304 repeats the entire process by generating another series of pulses according to the various stim sets. Thereby, a pulse is generated for each stim set according to the defined frequency of the stimulation program.

In certain embodiments for chronic pain and other neurological disorders, the stimulation parameters may comprise a burst stimulation at 6, 18, or 40 Hz consisting of 5 spikes with 1 ms pulse width, 1 ms interspike interval in combination with a 6, 18, or 40 Hz tonic stimulation interspersed between or around the bursts.

Figure 4:
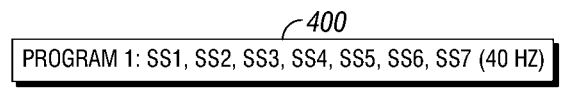
FIG. 4 depicts a stimulation program in which various parameters can be selected to define pulses of a burst and tonic stimulation pattern according to one representative embodiment.
Figure 5:
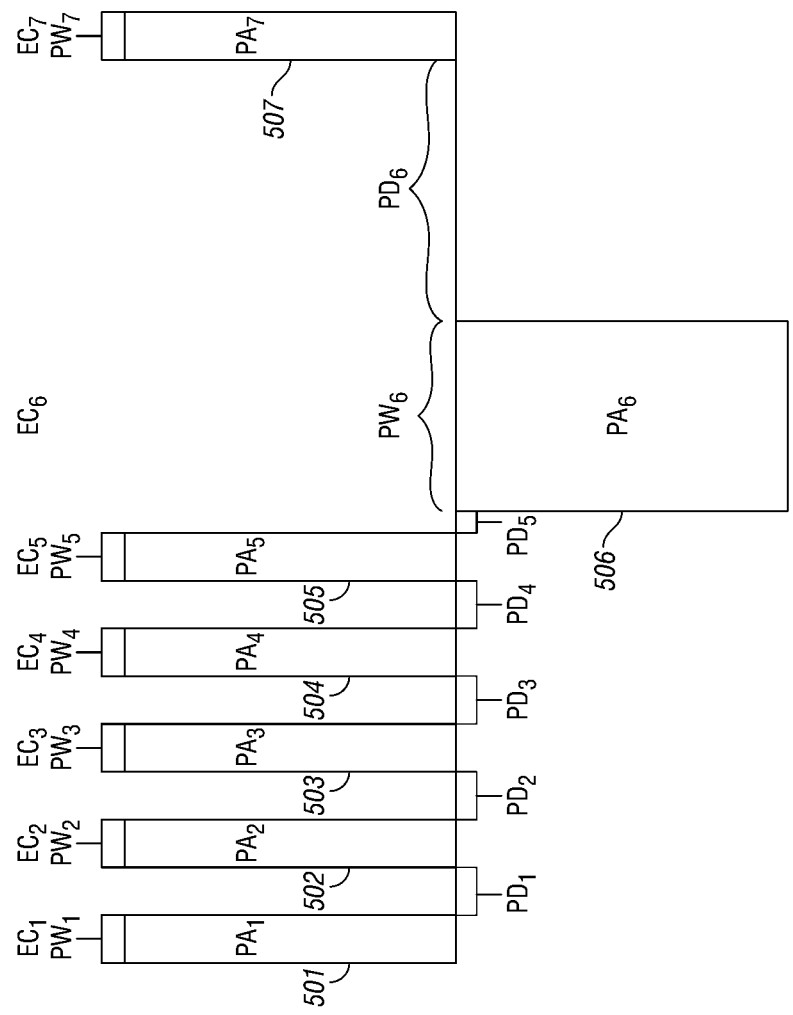
FIG. 5 depicts a stimulation program for defining burst and tonic stimulation according to one representative embodiment.

FIGS. 4 and 5 depict how stim sets and a stimulation program can be defined to generate burst and tonic stimulation according to one representative embodiment. FIG. 5 depicts a plurality of pulses 501-507. Pulses 501-505 are pulses of a discrete stimulation burst. The amplitude of pulses 501-505 can be defined in the amplitude parameters (shown as $PA_1$ through $PA_5$) of a plurality of stim sets. Each pulse lasts for an amount of time which is defined by the pulse width parameters of the plurality of stim sets (shown as $PW_1$ through $PW_5$). The pulses are output according the polarities of the electrode combinations (shown as $EC_1$ through $EC_5$) of the stim sets. Preferably, each electrode combination of the burst stimulus is the same. The inter-pulse or inter-spike intervals are defined by the delay parameters (shown as $PD_1$ through $PD_4$) of the stim sets.

A relatively small amount of delay can be defined to occur after the last pulse 505 of the burst stimulus before a charge balancing pulse 506 occurs. The electrode combination (shown as $EC_6$) of the charging balancing pulse 506 is preferably the opposite of the electrode combination used for each pulse of the burst stimulus. That is, for each anode of the burst stimulus, the charging balancing pulse 506 will configure those outputs as cathodes (and vice versa). Another delay occurs after the charging balancing pulses 506 as defined by the delay parameter (shown as $PD_6$) for the respective stim set.

The last pulse 507 is a stimulation pulse for the tonic stimulation. The amplitude of the tonic stimulation pulse is defined by the amplitude parameter (shown as $PA_7$) of the respective stim set. The duration of the tonic stimulation pulse 507 is defined by the pulse width parameter (shown as $PW_7$) of the respective stim set. The tonic stimulation pulse is output according to the electrode combination of the respective stim set (shown as $EC_7$). The electrode combination of the tonic stimulation may be the same as the electrode combination for the burst stimulation or may differ from the electrode combination for the burst stimulation. The delay parameter for the last stim set is not shown. Any suitable value could be assigned to the last stim set as long as the delay value permits a stimulation program to be repeated at an appropriate frequency.

FIG. 4 depicts stimulation program 400 for the stimulation pattern shown in FIG. 5. Stimulation program 400 identifies stim sets SS1-SS7 as belonging to the stimulation program. Accordingly, when stimulation program 400 is executed by IPG 200, stimulation pulses will be successively generated according to the parameters of the stim sets. Stimulation program 400 defines the frequency for the stimulation program, in this case, 40 Hz (although any suitable frequency could be selected). The burst stimulation and the tonic stimulation as defined by these stim sets will be repeated according to the defined frequency parameter.

Referring again to FIG. 3, the parameters associated with the various stim sets and stimulation programs are preferably communicated to IPG 200 using communication circuitry 305. For example, an external programming device may communicate the various parameters of the stim sets to IPG 200. Then, the external programming device may communicate parameters defining a given stimulation program according to the created stim sets. It shall be appreciated that the parameters shown in FIGS. 2-5 are by way of example only. Other parameters may be utilized to define burst and/or tonic stimulation. For example, burst parameters could be communicated from the programming device to IPG 200 (e.g., burst amplitude, inter-pulse or inter-spike interval, intra-burst spike repetition rate, pulse number, etc.), and IPG 200 could automatically configure parameters in its internal memory or registers in response thereto.

Figure 6:
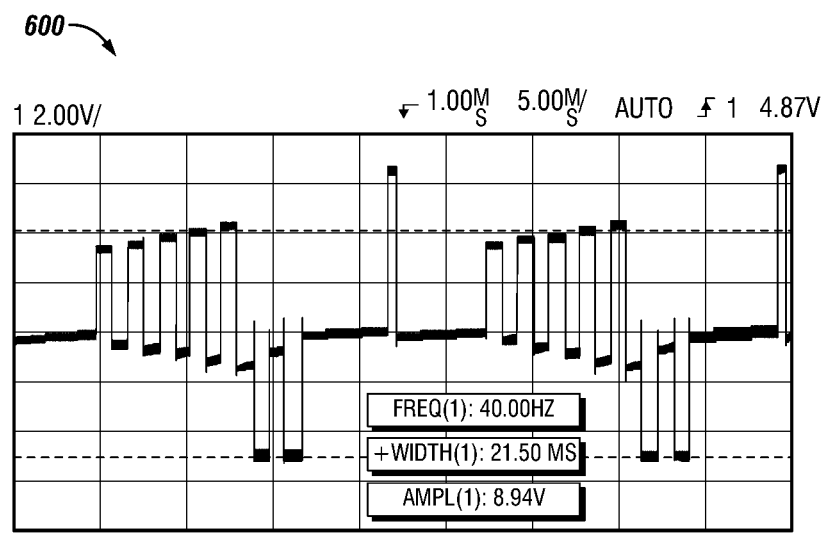
FIG. 6 depicts a combination of burst stimulation and tonic stimulation that can be used to treat a neurological condition or disorder according to one representative embodiment.

FIG. 6 depicts stimulation pattern 600 that includes a combination of burst stimulation and tonic stimulation that can be used to treat a neurological condition or disorder according to one representative embodiment. The individual pulses of stimulation pattern 600 could be manually defined by defining the pulse width, amplitude, delay parameters for respective stim sets and assembling the stim sets into a stimulation program. A manual process of defining stim sets in this manner can be time consuming during trial stimulation when an optimal stimulation pattern is sought for a patient's specific neurological condition or disorder. Accordingly, some embodiments provide a user-interface that is adapted to permit the creation of burst and tonic stimulation patterns in an efficient manner.

Figure 7:
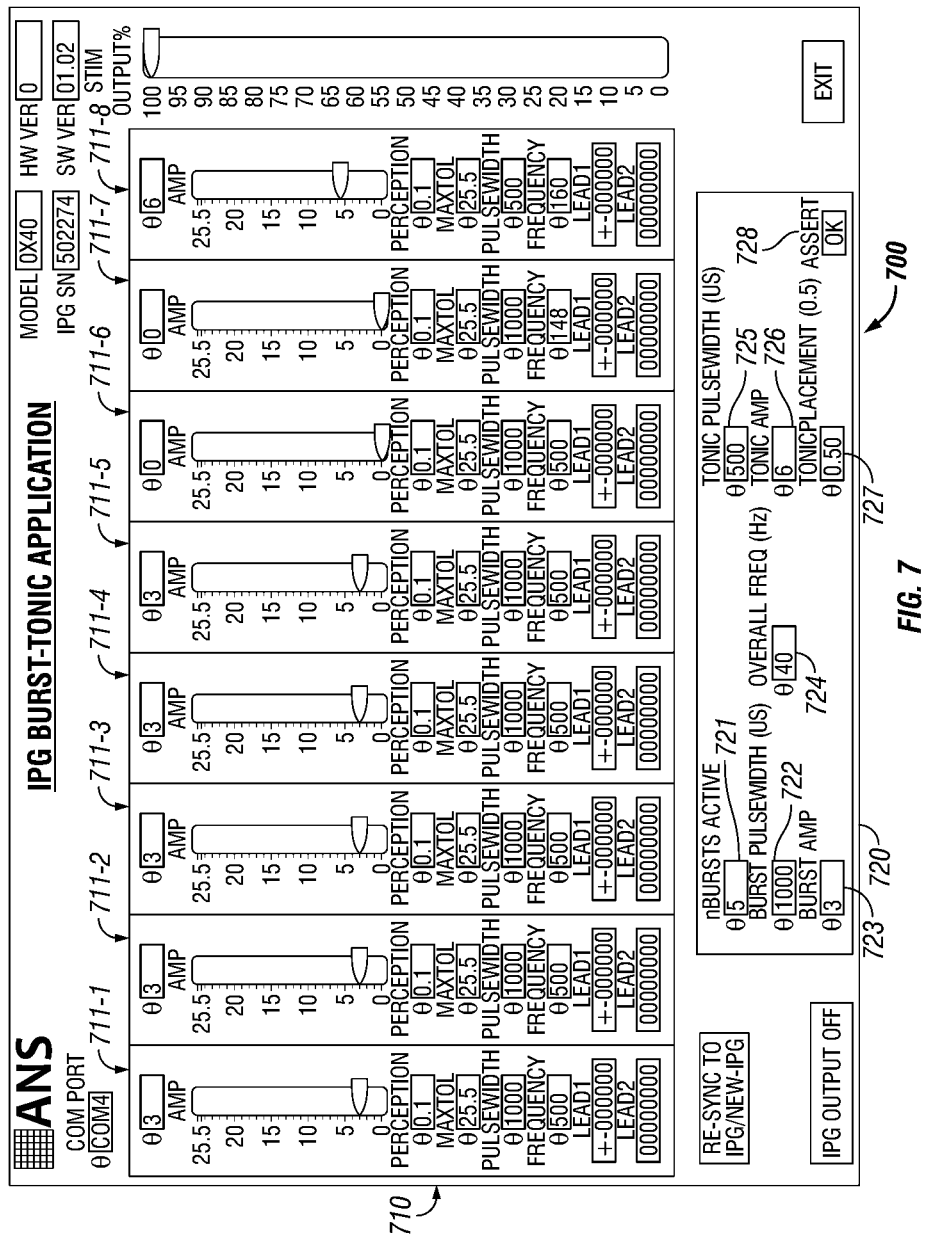
FIG. 7 depicts a user interface that can be employed to define burst and tonic stimulation according to one representative embodiment.

FIG. 7 depicts user interface 700 that can be employed to define burst and tonic stimulation according to one representative embodiment. User interface 700 can be implemented using suitable executable code stored on controller 250. Alternatively, the executable code could be resident on a separate system (e.g., a laptop computer) that uses controller 250 to communicate control signals to IPG 210.

User interface 700 comprises a first plurality of controls 710 and a second plurality 720 of controls. The first plurality 710 of controls allows selection of multiple stimulation parameters for a plurality of stimulation sets 711-1 through 711-8. For example, pulse amplitude and pulse width parameters can be controlled for each stimulation set 711. Conventional pulse calibration parameters, such a perception threshold value and a max tolerable limit, are preferably controllable for the stimulation sets 711 in the first plurality 710 of controls. Each stimulation set 711 is associated with a frequency parameter which defines an amount of time until the next stimulation set is selected. Alternatively, the frequency parameter could be equivalently represented by a time-interval delay value.

The second plurality 720 of controls allowing selection of multiple stimulation parameters defining a burst stimulation pattern and a tonic stimulation pattern to be interleaved for delivery to the patient. For example, the number of spikes in an individual burst of the stimulation pattern is controlled by control 721. The amplitude and pulse width of the individual burst pulses are controlled by controls 722 and 723, respectively. In one embodiment, pulse ramping may be automatically implemented. Specifically, pulse amplitudes may be automatically scaled from a beginning value to a maximum value in relation to the value input by the user into control 723. The amplitude and pulse width of the tonic stimulation to be interspersed between burst stimulation are controlled by controls 725 and 726, respectively. Control 727 allows the amount of time between the end of an individual burst and the occurrence of a tonic pulse to be controlled. The amount of time could be automatically calculated. For example, the midpoint between the end of the burst and the beginning of another burst could be selected for the tonic pulse and automatically calculated by software code in response to changes in other stimulation parameters. Control 724 controls the overall frequency of the combination of burst stimulation and tonic stimulation.

When a clinician provides input to change one or more parameter values in the second plurality 720 of controls, the user interface code preferably automatically recalculates and adjusts the parameter values for the respective stim sets 711-1 through 711-8 in the first plurality 710 of controls. For example, if the clinician modifies the number of pulses in an individual burst via control 721, the code automatically modifies the appropriate ones of stim sets 711-1 through 711-8 to reflect the pulse amplitude, pulse width, and an suitable pulse frequency. Also, the code automatically modifies frequency parameters (or equivalently delay parameters) associated with the other stim sets in view of the modification of the number of burst pulses so that the stimulation program is consistent with the overall stimulation frequency shown in control 724.

The clinician is thereby able to efficiently define a stimulation program including a combination of burst stimulation and tonic stimulation for a particular patient for the patient's particular neurological disorder or condition. If desired, the clinician can attempt to optimize the stimulation program by modifying the specific parameters of the stim sets 711 on an individual basis. The clinician could attempt to modify the amplitude and/or pulse width of individual pulses of the burst stimulation. Similarly, the clinician could modify the timing between individual pulses of the burst stimulation. Thus, the clinician is able to finely tune the stimulation program, if desired, while not being required to manually select each and every stimulation parameter of the stimulation program.

In some embodiments, when the clinician wishes to test or finalize the stimulation program, the clinician may select control 728. In response, the code associated with interface 700 communicates the stimulation set parameter values to the respective IPG. The IPG can then execute the stimulation program defined by the stimulation sets. The clinician may elicit feedback from the patient to determine whether the desired effect of the stimulation has been achieved (e.g., suppression of tinnitus, relief from the patient's chronic pain, etc.). Alternatively, various mechanisms may be utilized to determine whether the stimulation program is deemed effective without requiring the patient's conscious response (e.g., by measuring the evoked release of neurotransmitters for cortical or deep brain stimulation) depending upon the particular neurological condition or disorder being treated.

Any suitable neuronal site can be stimulated using combination of burst stimulation and tonic stimulation according to some representative embodiments. Suitable sites can include, for example, peripheral neuronal tissue and/or central neuronal tissue. Peripheral neuronal tissue can include a nerve root or root ganglion or any neuronal tissue that lies outside the brain, brainstem or spinal cord. Peripheral nerves can include, but are not limited to olfactory nerve, optic, nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccipital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves.

Central neuronal tissue includes brain tissue, spinal tissue or brainstem tissue. Brain tissue can include thalamus/subthalamus, basal ganglia, hippocampus, amygdala, hypothalamus, mammilary bodies, substantia nigra or cortex or white matter tracts afferent to or efferent from the abovementioned brain tissue, inclusive of the corpus callosum, more particularly, the brain tissue includes the auditory cortex and/or somatosensory cortex. Brainstem tissue can include the medulla oblongata, pons or mesencephalon, more particular the posterior pons or posterior mesencephalon, Lushka's foramen, and ventrolateral part of the medulla oblongata.

Spinal tissue can include the ascending and descending tracts of the spinal cord, more specifically, the ascending tracts of that comprise intralaminar neurons or the dorsal column. For example, the spinal tissue can include neuronal tissue associated with any of the cervical vertebral segments (C1, C2, C3, C4, C5, C6, C7 and C8) and/or any tissue associated with any of the thoracic vertebral segments (T1, T2, T3, T4, T5, T6, T7, T8, T9, T10, T11, 12) and/or any tissue associated with any of the lumbar vertebral segments (L1, L2, L3, L4. L5, L6) and/or any tissue associated with the sacral vertebral segments (S1, S2, S3, S4, S5).

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

What is claimed is:

1. A method for defining a stimulation program for electrical stimulation of a patient to treat chronic pain of a patient, the method comprising:
   providing a single screen user interface that comprises a first plurality of controls and a second plurality of controls, the first plurality of controls allowing selection of multiple stimulation parameters for application to multiple stimulation pulses of a complex pulse pattern, wherein (i) the first plurality of controls comprises controls for defining a burst subset of pulses within the complex pulse pattern and at least one tonic pulse within the complex pulse pattern and (ii) each control of the second plurality of controls allows selection of at least one stimulation parameter of one respective pulse within the complex pulse pattern, wherein (A) the complex pulse pattern produces a repeating pattern of multiple pulses at a fixed pulse rate followed in sequence by a first delay, a tonic pulse, and a second delay before repeating, and (B) the first delay and the second delay are constant in the repeating pattern;
   receiving user input in one or more of the first plurality of controls;
   automatically modifying parameters for respective pulses in the complex pulse pattern in response to receiving the user input in one or more of the first plurality of controls and automatically modifying values displayed in one or more controls of the second plurality of controls according to the modified parameters, wherein the automatically modifying values displayed in one or more controls of the second plurality of controls comprises automatically adjusting at least one of the first delay and the second delay in the complex pattern according to an overall pattern frequency rate defined using the first plurality of controls;
   creating a stimulation program employing the complex pulse pattern for electrical stimulation of the patient for storage in an implantable pulse generator; and
   operating the implantable pulse generator to deliver stimulation with the complex pulse pattern to the patient using spinal cord stimulation to treat chronic pain of the patient.

2. The method of claim 1 wherein the automatically modifying comprises:
   calculating a plurality of amplitudes for multiple pulses of the burst subset of pulses to define pulse ramping in response to selection of a single amplitude value for the burst stimulation in the first plurality of controls.

3. The method of claim 1 wherein the modified parameters are stored in a plurality of stimulation sets and the automatically modifying parameters for respective pulses comprises:
   modifying a plurality of parameter values for respective stimulation sets in response to selection of a number of pulses for the burst stimulation in the first plurality of controls.

4. The method of claim 1 wherein the plurality of first controls comprises a control for controlling a pulse width of pulses of the burst stimulation.

5. The method of claim 1 wherein the first plurality of controls comprises a control for controlling an amplitude of the tonic stimulation.

6. The method of claim 1 further comprising:
   generating a waveform display of the stimulation program.

7. The method of claim 1 wherein the modified parameters are stored in a plurality of stimulation sets and the method further comprising:
   communicating parameter values for stimulation sets of the stimulation program to an implantable pulse generator for execution of the stimulation program by the implantable pulse generator.

* * * * *